(12) United States Patent
Ukai et al.

(10) Patent No.: US 11,236,369 B2
(45) Date of Patent: Feb. 1, 2022

(54) FERMENTATION SYSTEM AND FERMENTATION METHOD USING SACCHARIDE SOLUTION

(75) Inventors: Nobuyuki Ukai, Tokyo (JP); Michio Nishiyama, Tokyo (JP); Hideo Suzuki, Tokyo (JP); Ryosuke Uehara, Tokyo (JP)

(73) Assignee: MITSUBISHI HEAVY INDUSTRIES POWER ENVIRONMENTAL SOLUTIONS, LTD., Yokohama (JP)

(*) Notice: Subject to any disclaimer, the term of this patent is extended or adjusted under 35 U.S.C. 154(b) by 0 days.

(21) Appl. No.: 13/700,753

(22) PCT Filed: Jul. 5, 2011

(86) PCT No.: PCT/JP2011/065375
§ 371 (c)(1),
(2), (4) Date: Nov. 29, 2012

(87) PCT Pub. No.: WO2012/005246
PCT Pub. Date: Jan. 12, 2012

(65) Prior Publication Data
US 2013/0078697 A1    Mar. 28, 2013

(30) Foreign Application Priority Data

Jul. 6, 2010 (JP) .............................. JP2010-154233

(51) Int. Cl.
*C12P 7/10* (2006.01)
*C12P 7/08* (2006.01)
(Continued)

(52) U.S. Cl.
CPC .............. *C12P 7/10* (2013.01); *C12M 21/12* (2013.01); *C12M 27/02* (2013.01); *C12M 33/16* (2013.01);
(Continued)

(58) Field of Classification Search
CPC ...... C12P 7/10; C12P 7/04; C12P 7/06; C12P 13/04; C12M 27/02; C12M 33/16; C12M 21/12; Y02E 50/10; Y02T 50/678
See application file for complete search history.

(56) References Cited

U.S. PATENT DOCUMENTS 3,985,725 A    10/1976  Lin
3,985,728 A    10/1976  Lin
(Continued)

FOREIGN PATENT DOCUMENTS

CA    2660990 A1    8/2009
CA    2666152 A1    4/2010
(Continued)

OTHER PUBLICATIONS

Gribovskaya et al. "Extraction of Mineral Elements from Inedible Wastes of Biological Components of a Life-Support System and Their Utilization for Plant Nutrition" Adv. Space Res. vol. 18, No. 4/5 pp. 93-97 (Year: 1996).*
(Continued)

*Primary Examiner* — Blaine Lankford
*Assistant Examiner* — Lauren K Van Buren
(74) *Attorney, Agent, or Firm* — Westerman, Hattori, Daniels & Adrian, LLP

(57) ABSTRACT

An alcohol production system that produces alcohol by alcoholic fermentation using a saccharide solution, including an alcoholic fermentation vessel in which the saccharide solution is fermented by adding yeast to produce alcohol, which is an organic feedstock, and a biomass-hydrothermally-treated-product adding means that adds a biomass hydrothermally-treated product obtained by hydrothermally treating a biomass feedstock to the alcoholic fermentation vessel. The alcohol production system can improve alco-
(Continued)

holic fermentation efficiency and realize cost reduction without adding only a mineral salt from outside.

1 Claim, 9 Drawing Sheets

(51) Int. Cl.
| | |
|---|---|
| *C12P 19/00* | (2006.01) |
| *C13K 1/02* | (2006.01) |
| *C12M 1/00* | (2006.01) |
| *C12P 7/04* | (2006.01) |
| *C12P 7/06* | (2006.01) |
| *C12P 13/04* | (2006.01) |
| *C12M 1/06* | (2006.01) |
| *C12M 1/26* | (2006.01) |

(52) U.S. Cl.
CPC ............... *C12P 7/04* (2013.01); *C12P 7/06* (2013.01); *C12P 13/04* (2013.01); *Y02E 50/10* (2013.01); *Y02T 50/678* (2013.01)

(56) References Cited

U.S. PATENT DOCUMENTS

| | | | |
|---|---|---|---|
| 4,023,982 | A | 5/1977 | Knauth |
| 4,152,197 | A | 5/1979 | Lindahl et al. |
| 4,650,689 | A | 3/1987 | Hedrick |
| 4,746,401 | A | 5/1988 | Roberts et al. |
| 4,859,322 | A | 8/1989 | Huber |
| 5,348,871 | A | 9/1994 | Scott et al. |
| 5,411,594 | A * | 5/1995 | Brelsford ............... B01J 19/242 127/1 |
| 5,424,417 | A | 6/1995 | Torget et al. |
| 5,466,108 | A | 11/1995 | Piroska |
| 6,022,419 | A | 2/2000 | Torget et al. |
| 6,419,788 | B1 | 7/2002 | Wingerson |
| 8,123,864 | B2 | 2/2012 | Christensen et al. |
| 8,163,517 | B2 | 4/2012 | Genta et al. |
| 9,102,956 | B2 | 8/2015 | Genta et al. |
| 2007/0231869 | A1 | 10/2007 | Holmgren et al. |
| 2007/0259412 | A1 | 11/2007 | Belanger et al. |
| 2008/0026431 | A1 | 1/2008 | Saito et al. |
| 2008/0032344 | A1 | 2/2008 | Fallavollita |
| 2008/0044891 | A1 * | 2/2008 | Kinley ............... C12M 35/04 435/289.1 |
| 2008/0299628 | A1 | 12/2008 | Hallberg et al. |
| 2008/0299630 | A1 * | 12/2008 | Maclennan ............ C12P 7/06 435/161 |
| 2009/0311752 | A1 * | 12/2009 | Bodie ..................... C12N 1/22 435/72 |
| 2010/0108567 | A1 | 5/2010 | Medoff |
| 2010/0184176 | A1 | 7/2010 | Ishida et al. |
| 2010/0269990 | A1 | 10/2010 | Dottori et al. |
| 2010/0285574 | A1 * | 11/2010 | Genta et al. .............. 435/289.1 |
| 2010/0330633 | A1 * | 12/2010 | Walther .................. C12P 7/28 435/150 |
| 2010/0330638 | A1 | 12/2010 | Aita et al. |
| 2011/0003348 | A1 | 1/2011 | Genta et al. |
| 2011/0079219 | A1 | 4/2011 | McDonald et al. |
| 2011/0314726 | A1 | 12/2011 | Jameel et al. |
| 2012/0006320 | A1 | 1/2012 | Nguyen |
| 2012/0315683 | A1 | 12/2012 | Mosier et al. |
| 2014/0004571 | A1 | 1/2014 | Garrett et al. |
| 2014/0273127 | A1 | 9/2014 | Fuchs et al. |

FOREIGN PATENT DOCUMENTS

| | | | |
|---|---|---|---|
| CA | 2 750 754 | A1 | 1/2012 |
| CA | 2654306 | C | 10/2013 |
| EP | 0 098 490 | A2 | 1/1984 |
| JP | 09-507386 | A | 7/1997 |
| JP | 11-506934 | A | 6/1999 |
| JP | 2001-170601 | A | 6/2001 |
| JP | 2002-059118 | A | 2/2002 |
| JP | 2002-516115 | A | 6/2002 |
| JP | 2003-311141 | A | 11/2003 |
| JP | 2005-27541 | A | 2/2005 |
| JP | 2005-168335 | A | 6/2005 |
| JP | 2005168335 | * | 6/2005 |
| JP | 2005-205252 | A | 8/2005 |
| JP | 2005-229821 | A | 9/2005 |
| JP | 2006-036977 | A | 2/2006 |
| JP | 2006-136263 | A | 6/2006 |
| JP | 2006-223152 | A | 8/2006 |
| JP | 2006-289164 | A | 10/2006 |
| JP | 2007-112880 | A | 5/2007 |
| JP | 2007-202560 | A | 8/2007 |
| JP | 2007-301472 | A | 11/2007 |
| JP | 2008-054608 | A | 3/2008 |
| JP | 2008-104452 | A | 5/2008 |
| JP | 2008-278825 | A | 11/2008 |
| JP | 2009-183153 | A | 8/2009 |
| JP | 2009-183154 | A | 8/2009 |
| JP | 2009-183805 | A | 8/2009 |
| JP | 2009-183806 | A | 8/2009 |
| JP | 2010-017084 | A | 1/2010 |
| JP | 4764527 | B1 | 9/2011 |
| JP | 4764528 | B1 | 9/2011 |
| WO | 84/003304 | A1 | 8/1984 |
| WO | 95/17517 | A1 | 6/1995 |
| WO | 96/40970 | A1 | 12/1996 |
| WO | 99/61646 | A1 | 12/1999 |
| WO | WO2009096062 | * | 6/2009 |
| WO | 2009/096060 | A1 | 8/2009 |
| WO | 2009096061 | A1 | 8/2009 |
| WO | 2009/124240 | A1 | 10/2009 |
| WO | 2010/038302 | A1 | 4/2010 |
| WO | WO2010038302 | * | 8/2010 |
| WO | 2013/082616 | A2 | 6/2013 |

OTHER PUBLICATIONS

Ibanez et al. "Subcritical Water Extraction of Antioxidant Compounds from Rosemary Plants" Journal of Agric. Food Chem. 2003, 51, 375-382 (Year: 2003).*
Written Opinion of PCT/JP2011/065375, dated Sep. 13, 2011 (English Translation Only).
Genda, Minoru et al., "Suinetsu Bunkaiho to Koso Bunkaiho o Kumiawaseta Nogyo Zansa To no Cellulose Biomass no Tei Cost Toka Gijutsu no Kaihatsu", Feb. 2010, Heisei 21 Nendo Biomass Energy Kanren Jigyo Seika Hokokukai, pp. 55-69; cited in ISR.
International Search Report of PCT/JP2011/065375, dated Sep. 13, 2011.
Written Opinion of PCT/JP2011/065375, dated Sep. 13, 2011.
U.S. Non-Final Office Action dated Dec. 17, 2013, issued in related U.S. Appl. No. 13/203,929 (23 pages).
U.S. Non-Final Office Action dated Dec. 16, 2013, issued in related U.S. Appl. No. 13/132,034 (29 pages).
Gregg, D. et al., "Bioconversion of Lignocellulosic Residue to Ethanol: Process Flowsheet Development", Biomass and Bioenergy, 1995, vol. 9, No. 1-5, pp. 287-302, Cited in U.S. Office Action dated Dec. 17, 2013.
Canadian Office Action dated Nov. 8, 2013, issued in Canadian Patent Application No. 2,801,383 (2 pages).
Indonesian Notice of Allowance dated Nov. 15, 2013, issued in Indonesian Patent Application No. W-00201002623, w/English translation, (5 pages).
U.S. Non-Final Office Action dated Jan. 30, 2014 issued in related U.S. Appl. No. 12/438,792 (39 pages).
Canadian Notice of Allowance dated Jan. 13, 2014, issued in Canadian Patent Application No. 2,744,522 (1 page).
U.S. Non-Final Office Action dated Jan. 30, 2014, issued in related U.S. Appl. No. 13/578,116 (22 pages).
U.S. Final Office Action dated Feb. 13, 2014, issued in U.S. Appl. No. 12/865,273 (26 pages).
Liu, Chaogang, et al., "Continuous Fermentation of Hemicellulose Sugars and Cellulose to Ethanol", International Symposia on Alco-

(56) References Cited

OTHER PUBLICATIONS hol Fuels, (2005), pp. 1-28 (cited in U.S. Final Office Action dated Feb. 13, 2014, issued in U.S. Appl. No. 12/865,273).
U.S. Non-Final Office Action dated Mar. 10, 2014, in U.S. Appl. No. 13/782,545 (27 pages).
Decision of a Patent Grant dated Mar. 4, 2014, issued in JP2009-252201 (corresponding to U.S. Appl. No. 12/443,515), w/English translation (4 pages).
Decision of a Patent Grant dated Mar. 4, 2014, issued in JP2009-245963 (corresponding to U.S. Appl. No. 12/438,792) w/English translation (4 pages).
Australian Notice of Acceptance dated Mar. 17, 2014, issued in Australian U.S. Appl. No. 13/578,116 (corresponding to U.S. Appl. No. 13/578,116) (2 pages).
U.S. Office Action dated Apr. 14, 2014, issued in U.S. Appl. No. 12/443,515 (16 pages).
Kumagai Satoshi et al. "Fractionation and Saccharification of Cellulose and Hemicellulose in Rice Hull by Hot-Compressed-Water Treatment with Two-Step Heating", Journal of the Japan Institute of Energy, Dec. 1, 2003 (Dec. 1, 2003), vol. 83, pp. 776-781.
Canadian Notice of Allowance dated Aug. 22, 2013, issued in Canadian Patent Application No. 2666152.
Canadian Notice of Allowance dated Aug. 22, 2013, issued in Canadian Patent Application No. 2713529.
U.S. Office Action dated Oct. 28, 2013, issued in U.S. Appl. No. 12/443,515.
U.S. Office Action dated Aug. 19, 2013 issued in U.S. Appl. No. 13/578,116.
Arroyo-Lopez, F.N. et al., "Effects of temperature, pH and sugar concentration on the growth parameters of *Saccharomyces cerevisiae*, S. kudriavzevii and their interspecific hybrid", International Journal of Food Microbiology, vol. 131, pp. 120-127 (2009).
Turton, L.J. et al., "Effect of Glucose Concentration in the Growth Medium Upon Neutral and Acidic Fermentation End-products of Clostridium Bifermentans, Clostridium Sporogenes and Peptostreptococcus Anaerobius", J. Med. Microbiol., vol. 16, pp. 61-67 (1983).
Dien, B.S. et al., "Fermentation of hexose and pentose sugars using a novel ethanologenic *Escherichia coli* strain", Enzyme and Microbial Technology, vol. 23, pp. 366-371 (1998).
U.S. Office Action dated Oct. 3, 2013 issued in U.S. Appl. No. 13/782,545.
International Search Report dated Jul. 3, 2012 issued in International Application No. PCT/JP2012/058460 (corresponds to U.S. Appl. No. 14/381,511).
Written Opinion of the International Searching Authority dated Jul. 3, 2012 issued in International Application No. PCT/JP2012/058460 (corresponds to U.S. Appl. No. 14/381,511).
Decision of a Patent Grant dated Nov. 12, 2013, issued in Japanese Patent Application No. 2013-536355, w/English translation (corresponds to U.S. Appl. No. 14/381,511) (4 pages).
U.S. Office Action dated Apr. 24, 2015, issued in U.S. Appl. No. 14/381,511 (20 pages).
Notice of Allowance and Fee(s) Due dated Feb. 17, 2015, issued in U.S. Appl. No. 13/782,545 (20 pages).
U.S. Office Action dated Mar. 19, 2015, issued in U.S. Appl. No. 13/121,969 (21 pages).
U.S. Office Action dated Mar. 13, 2015, issued in U.S. Appl. No. 13/722,385 (41 pages).
Notice of Allowance and Fee(s) Due dated Apr. 2, 2015, issued in U.S. Appl. No. 13/132,040 (17 pages).
U.S. Office Action dated Mar. 31, 2015, issued in U.S. Appl. No. 12/865,273 (25 pages).
U.S. Office Action dated May 13, 2015, issued in U.S. Appl. No. 12/438,792 (11 pages).
Canadian Office Action dated Mar. 31, 2014, issued in Canadian Patent Application No. 2,750,753 (3 pages) (corresponding to U.S. Appl. No. 13/203,929).
U.S. Final Office Action dated Jun. 3, 2014, issued in U.S. Appl. No. 13/203,929 (22 pages).
U.S. Final Office Action dated Jul. 3, 2014, issued in U.S. Appl. No. 13/578,116 (17 pages).
U.S. Final Office Action dated Aug. 18, 2014, issued in U.S. Appl. No. 13/132,034 (30 pages).
U.S. Final Office Action dated Jun. 13, 2014, issued in U.S. Appl. No. 12/438,792 (26 pages).
U.S. Non-Final Office Action dated Aug. 27, 2014, issued in U.S. Appl. No. 13/132,040 (53 pages).
U.S. Final Office Action dated Jul. 22, 2014, issued in U.S. Appl. No. 12/443,515 (13 pages).
Indonesian Office Action dated Nov. 7, 2014, issued in Indonesian Patent Application No. W00200902414, w/English translation (corresponds to U.S. Appl. No. 12/438,792) (6 pages).
Indonesian Office Action dated Nov. 14, 2014, issued in Indonesian Patent Application No. W00201102352, w/English translation (corresponds to U.S. Appl. No. 13/121,969) (7 pages).
Genda, M. et al., "Suinetsu Bunkaiho to Koso Bunkaiho o Kumiawaseta Nogyo Zansa To no Cellulose Biomass no Tei CostToka Gijutsu no Kaihatsu", Heisei 21 Nendo Biomass Energy Kanren Jigyo Seika Hokokukai, Feb. 11, 2010, pp. 55-69, URL, http://www.nedo.go.jp/events/report/FF_00003.html, Cited in JP Office Action dated Oct. 14, 2014.
Lehrburger, E. "Developing biorefineries to produce energy, ethanol and other industrial products", PureVision Technology, Inc., Alternative Energy Conference, Mar. 3, 2005, pp. 1-26, Cited in U.S. Office Action dated Nov. 6, 2014.
U.S. Office Action dated Sep. 30, 2014, issued in U.S. Appl. No. 13/782,545 (43 pages).
U.S. Office Action dated Nov. 6, 2014, issued in U.S. Appl. No. 12/865,273 (27 pages).
Japanese Office Action dated Oct. 14, 2014, issued in corresponding Japanese Patent Application No. 2010-154233, with English Translation (7 pages).
U.S. Office Action dated Dec. 5, 2014, issued in U.S. Appl. No. 13/121,969.
Canadian Notice of Allowance dated Dec. 5, 2014, issued in Canadian Patent Application No. 2750754 (corresponds to U.S. Appl. No. 13/203,848).
Indonesian Office Action dated Oct. 29, 2014, issued in Indonesian Patent Application No. W00201103522 (corresponds to U.S. Appl. No. 13/203,929), w/English translation.
U.S. Notice of Allowance dated Nov. 5, 2014, issued in U.S. Appl. No. 12/443,515.
U.S. Office Action dated Dec. 26, 2014, issued in U.S. Appl. No. 13/132,040.
Final Office Action dated Aug. 6, 2015, issued in U.S. Appl. No. 14/381,511 (14 pages).
Notice of Allowance dated Aug. 19, 2015, issued in U.S. Appl. No. 12/438,792 (12 pages).
Notice of Allowance and Fees Due, dated Aug. 12, 2015, issued in U.S. Appl. No. 13/578,116 (48 pages).
Non-Final Office Action dated Aug. 21, 2015, issued in U.S. Appl. No. 13/203,929 (18 pages).
Notice of Allowance dated Jul. 6, 2015, issued in Indonesian application No. W-00201103522, counterpart of U.S. Appl. No. 13/203,929 (4 pages).
Office Action dated Jul. 10, 2015, issued in counterpart Australian Patent Application No. 2012374915 (5 pages).
Notice of Allowance dated Dec. 21, 2015 issued in U.S. Appl. No. 14/381,511. (11 pages).
Notice of Allowance dated Mar. 14, 2016, issued in U.S. Appl. No. 13/121,969. (12 pages).
Office Action dated Mar. 30, 2016, issued in counterpart Indonesian Patent Application No. W-00201102351, with English translation. (4 pages).
Notice of Allowance dated May 5, 2016, issued in U.S. Appl. No. 13/203,848. (23 pages).
Notice of Allowance dated Feb. 3, 2016, issued in U.S. Appl. No. 13/578,116. (17 pages).
Notice of Allowance dated Mar. 30, 2016, issued in Indonesian Patent Application No. W00200902414, with English translation. (4 pages).

(56) References Cited

OTHER PUBLICATIONS

Office Action dated Sep. 25, 2015 issued in U.S. Appl. No. 13/132,034, (39 pages).
Office Action dated Sep. 28, 2015 issued in U.S. Appl. No. 13/203,848, (34 pages).
Notice of Allowance dated Sep. 30, 2015 issued in counterpart Canadian patent application No. CA patent application No. 2,791,665, (1 page).
Notice of Allowance dated Nov. 10, 2015 issued in counterpart Japanese patent application No. JP2010-154233, with English translation (5 pages).
Office Action dated Sep. 29, 2016, issued in co-pending U.S. Appl. No. 14/411,473 (English; 33 pages; w/ PTO-892 and returned PTO/SB/08 forms).
Notice of Allowance dated Aug. 8, 2016, issued in Indonesian Patent Application No. W00201102351, with English translation. (4 pages).
Notice of Allowance dated Oct. 5, 2016, issued in U.S. Appl. No. 13/722,385. (5 pages).
Non-Final Office Action dated Oct. 7, 2016, issued in U.S. Appl. No. 13/132,034. (19 pages).
Carrasco, J.E. et al., "Effects of Dilute Acid and Steam Explosion Pretreatments on the Cellulose Structure and Kinetics of Cellulosic Fraction Hydrolysis by Dilute Acids in Lignocellulosic Materials", Applied Biochemistry and Biotechnology, 1994, 45/46, pp. 23-34; cited in U.S. Office Action dated Sep. 28, 2018.
Final Office Action dated Sep. 28, 2018, issued in U.S. Appl. No. 12/865,273, (18 pages).
Mosier, N. et al., "Features of promising technologies for pretreatment of lignocellulosic biomass", Bioresource Technology, 2005, vol. 96, pp. 673-686; cited in Brazilian Office Action dated May 8, 2018.
Petersen, M. Ø. et al., "Optimization of hydrothermal pretreatment of wheat straw for production of bioethanol at low water consumption without addition of chemicals", Biomass and Biotechnology, 2009, vol. 33, pp. 834-840; cited in Brazilian Office Action dated May 8, 2018.
Silva, V.D.N., "Estudos de pré-tratamento e sacarificação enzimática de resíduos agroindustriais como etapas no processo de obtenção de etanol celulósico", Dissertagao de M.Sc., USP Lorena, SP, Brasil, 2009; cited in Brazilian Office Action dated May 8, 2018. (113 pages).
Office Action dated May 8, 2018, issued in counterpart Brazilian Application No. BR112012030802-5, with English translation. (17 pages).
Non-Final Office Action dated Mar. 28, 2019, issued in U.S. Appl. No. 12/865,273. (11 pages).
Kohlmann, K. L. et al., "Enhanced Enzyme Activities on Hydrated Lignocellulosic Substrates", In: Saddler, J.N., Penner, M. H. (Eds.), Enzymatic Degradation of Insoluble Carbohydrates. ACS Publishing, 1995, pp. 237-255; cited in Non-Final Office Action of U.S. Appl. No. 12/865,273 dated Mar. 28, 2019.
Final Office Action dated Nov. 13, 2019, issued in U.S. Appl. No. 12/865,273. (26 pages).
Zufle et al., "Catalytic combustion in a reactor with periodic flow reversal. Part 2. Steady-state reactor model", Chemical Engineering and Processing, (1997), 36, pp. 341-352, cited in Final Office Action dated Nov. 13, 2019. (12 pages).

\* cited by examiner

FERMENTATION SYSTEM AND FERMENTATION METHOD USING SACCHARIDE SOLUTION

FIELD

The present invention relates to a fermentation system using a saccharide solution that improves fermentation efficiency at the time of causing alcoholic fermentation by using a saccharide solution, for example.

BACKGROUND

Conventionally, a production technique of ethanol or the like in which after biomass such as wood is saccharified by diluted sulfuric acid or concentrated sulfuric acid, the biomass is solid-liquid separated, and a liquid phase is neutralized and used as raw materials for ethanol fermentation or the like has been used in practice (Patent Literature 1, Patent Literature 2).

Furthermore, it is also conceivable to produce chemical raw materials (for example, lactic acid fermentation), using saccharide as a starting material.

The biomass refers to accumulation of organisms or organic matters derived from organisms integrated in a circulatory system of materials of the global biosphere (Japanese Industrial Standards Committee, "Biotechnology-Vocabulary", JIS K 3600 1258, Oct. 1, 2010).

As a method of improving alcoholic fermentation, for example, it has been proposed to use yeast that is rich in minerals or concentrated with minerals as a nutrient source for alcoholic fermentation (Patent Literature 3).

CITATION LIST

Patent Literatures

Patent Literature 1: Japanese Patent Application National Publication No. H9-507386
Patent Literature 2: Japanese Patent Application National Publication No. H11-506934
Patent Literature 3: Japanese Patent Application National Publication No. 2002-516115

SUMMARY

Technical Problem

However, in the proposal in Patent Literature 3, there is a problem that a mineral salt needs to be supplied from outside as a method of concentrating minerals. That is, although there are methods such as directly supplying a mineral salt to an alcoholic fermentation vessel and indirectly supplying thereto via yeast cultivation, addition of a mineral salt from outside becomes essential in either method.

Accordingly, there has been a strong demand for a fermentation system and a fermentation method using a saccharide solution capable of improving fermentation efficiency and realizing cost reduction at the time of fermenting, for example, alcohol from a saccharide solution, without adding only a mineral salt from outside.

The present invention has been achieved to solve the above problems, and an object of the present invention is to provide a fermentation system and a fermentation method using a saccharide solution capable of improving fermentation efficiency at the time of fermenting, for example, alcohol from a saccharide solution.

Solution to Problem

In order to solve the problems, according to a first aspect of the invention, there is provided a fermentation system using a saccharide solution, which is an alcohol production system that produces alcohol by fermentation of the saccharide solution, the fermentation system including: a fermentation vessel for fermenting the saccharide solution by adding yeast so as to produce an organic feedstock; and a biomass-hydrothermally-treated-product adding unit for adding biomass hydrothermally-treated product obtained by hydrothermally treating a biomass feedstock to the fermentation vessel.

According to a second aspect of the invention, there is provided a fermentation system using a saccharide solution according to the first aspect, wherein the biomass hydrothermally-treated product is either one or both of a solid residual fraction and a hydrothermally treated fraction.

According to a third aspect of the invention, there is provided a fermentation system using a saccharide solution according to the first or second aspect, including an addition piping for adding either one or both of a fermentation residual fraction and a distillation residual fraction to the fermentation vessel individually or in addition to the biomass hydrothermally-treated product.

According to a fourth aspect of the invention, there is provided a fermentation system using a saccharide solution according to the third aspect, wherein either one or both of the alcoholic fermentation residual fraction and the distillation residual fraction are hydrothermally treated by a hydrothermal decomposition device, and a hydrothermally treated product is then added to the fermentation vessel.

According to a fifth aspect of the invention, there is provided a fermentation system using a saccharide solution according to the first aspect, wherein the biomass hydrothermally-treated product is a saccharified feedstock of an organic-feedstock production system using a cellulosic biomass feedstock.

According to a sixth aspect of the invention, there is provided a fermentation system using a saccharide solution according to the fifth aspect, including an addition line for adding a treatment residue of the organic-feedstock production system using the cellulosic biomass feedstock to the fermentation vessel.

According to a seventh aspect of the invention, there is provided a fermentation system using a saccharide solution according to the fifth or sixth aspect, wherein
the organic-feedstock production system using the cellulosic biomass feedstock includes: a hydrothermal decomposition device for hydrothermally decomposing a biomass feedstock by feeding the biomass feedstock into countercurrent contact with pressurized hot water and by transferring a lignin component and a hemicellulose component into pressurized hot water, so as to separate the lignin component and the hemicellulose component from a biomass solid; a first enzymatic saccharification tank for treating cellulose in a solid residual fraction discharged from the hydrothermal decomposition device with an enzyme so as to enzymatically decompose cellulose into a saccharide solution containing hexose with a first enzyme; and a first fermentation device for producing either one of alcohol, petroleum substitutes, or amino acids by fermentation treatment, by using a first saccharide solution obtained in the first enzymatic saccharification tank.

According to a eighth aspect of the invention, there is provided a fermentation system using a saccharide solution according to the seventh aspect, further including: a second enzymatic decomposition device for treating the hemicellulose component in a hydrothermally extracted fraction from the hydrothermal decomposition device with an enzyme so as to enzymatically decompose hemicellulose into a saccharide solution containing pentose; and a second fermentation device for producing either one of alcohol, petroleum substitutes, or amino acids by fermentation treatment, by using a second saccharide solution obtained by the second enzymatic decomposition device.

According to a ninth aspect of the invention, there is provided a fermentation system using a saccharide solution according to the seventh aspect, further including: a sulfuric-acid decomposition device for decomposing the hemicellulose component in a hydrothermally extracted fraction from the hydrothermal decomposition device with sulfuric acid into a second saccharide solution containing pentose; and a second fermentation device for producing either one of alcohol, petroleum substitutes, or amino acids by fermentation treatment, by using a second saccharide solution obtained by the sulfuric-acid decomposition device.

According to a tenth aspect of the invention, there is provided a fermentation system using a saccharide solution according to the seventh, wherein the hydrothermal decomposition device includes: a hydrothermal decomposition device body for gradually moving a biomass feedstock in a consolidation state; and a hot-water supply unit for supplying pressurized hot water into the hydrothermal decomposition device body, and wherein the biomass feedstock and the pressurized hot water are hydrothermally decomposed while being brought into countercurrent contact with each other, the lignin component and the hemicellulose component are transferred into the pressurized hot water, so as to separate the lignin component and the hemicellulose component from the biomass feedstock, thereby obtaining a hydrothermally extracted fraction containing the lignin component and the hemicellulose component and a solid residual fraction containing cellulose.

According to a eleventh aspect of the invention, there is provided a fermentation method using a saccharide solution for producing an organic feedstock by fermenting the saccharide solution, the fermentation method including: adding a biomass hydrothermally-treated product obtained by hydrothermally treating a biomass feedstock to a fermentation vessel so as to ferment the organic feedstock.

According to a twelfth aspect of the invention, there is provided a fermentation method using a saccharide solution according to the eleventh aspect, wherein the biomass hydrothermally-treated product is either one or both of a hydrothermally treated fraction and a solid residual fraction.

According to a thirteenth aspect of the invention, there is provided a fermentation method using a saccharide solution according to the eleventh or twelfth aspect, wherein the biomass hydrothermally-treated product is a saccharified feedstock of an organic-feedstock production system using a cellulosic biomass feedstock.

According to a fourteenth aspect of the invention, there is provided a fermentation method using a saccharide solution according to the eleventh or twelfth aspect, wherein either one or both of a fermentation residual fraction and a distillation residual fraction are added to the fermentation vessel individually or in addition to the biomass hydrothermally-treated product.

According to a fifteenth aspect of the invention, there is provided a fermentation method using a saccharide solution according to the fourteenth aspect, wherein either one or both of the alcoholic fermentation residual fraction and the distillation residual fraction are hydrothermally treated, and then added to an alcoholic fermentation vessel.

According to a sixteenth aspect of the invention, there is provided a fermentation method using a saccharide solution according to the thirteenth aspect, wherein a treatment residue of the organic-feedstock production system using the cellulosic biomass feedstock is added to the fermentation vessel.

Advantageous Effects of Invention

According to the present invention, alcoholic fermentation efficiency can be improved and cost reduction can be realized without adding only a mineral salt from outside.

DESCRIPTION OF EMBODIMENTS

The present invention will be explained below in detail with reference to the accompanying drawings. The present invention is not limited to the following embodiments. In addition, constituent elements in the following embodiments include those that can be easily anticipated by persons skilled in the art or that are substantially equivalent.

First Embodiment

Figure 1:
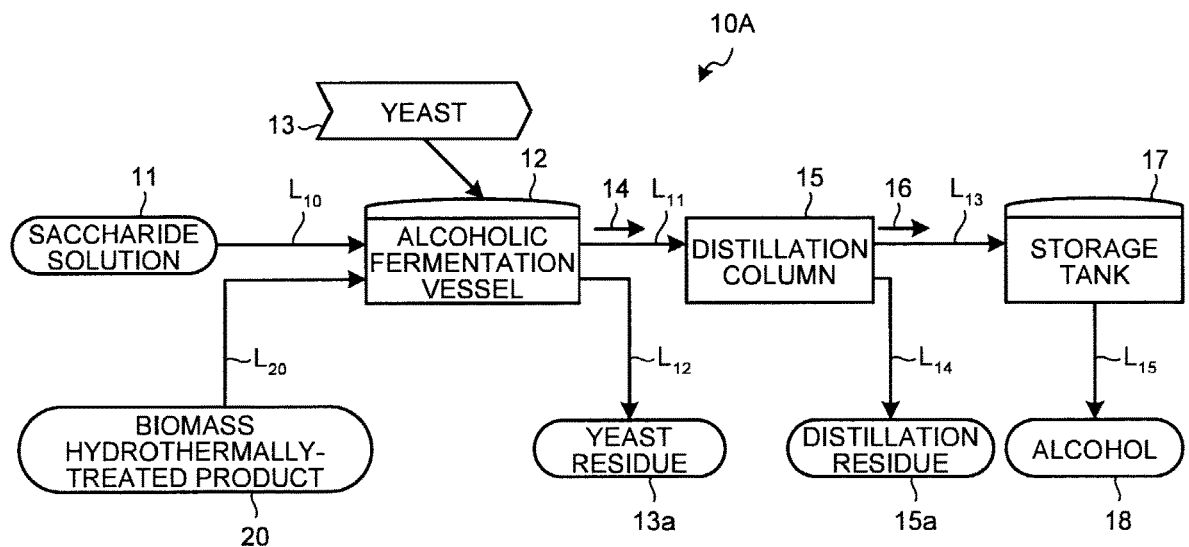
FIG. 1 is a schematic diagram of an alcohol production system according to a first embodiment.

An alcohol production system and an alcohol production method are exemplified and explained as a fermentation system and a fermentation method using a saccharide solution according to an embodiment of the present invention with reference to the drawings. FIG. 1 is a schematic diagram of an alcohol production system according to a first embodiment.

As shown in FIG. 1, an alcohol production system 10A according to the first embodiment produces alcohol by fermentation of a saccharide solution 11. The alcohol production system 10A includes an alcoholic fermentation vessel 12 in which the saccharide solution 11 is fermented by adding yeast 13, thereby fermenting alcohol, which is an organic feedstock, and a biomass-hydrothermally-treated-product adding means (not shown) that adds a biomass hydrothermally-treated product 20 obtained by hydrothermally treating a biomass feedstock to the alcoholic fermentation vessel 12 through a supply piping $L_{20}$.

The saccharide solution 11, which is an alcoholic fermentation feedstock, is fed to the alcoholic fermentation vessel 12 through a saccharide-solution supply piping $L_{10}$, and fermentation treatment is performed under predetermined conditions by the yeast 13 to be added.

For example, as the saccharide solution 11, syrup, a saccharide solution from sugar cane, a saccharide solution from cassava, and a saccharide solution from corn can be exemplified. However, the present invention is not limited thereto.

An alcoholic fermentation liquor 14 produced by alcoholic fermentation is fed to a distillation column 15 through a fermentation-liquor supply piping $L_{11}$, where distillation is performed.

A distilled distillate 16 is refined by a refinery (not shown), and fed to a storage tank 17 through an alcohol supply piping $L_{13}$. Alcohol 18 as a product is supplied from the storage tank 17, as required, through a supply piping $L_{15}$.

A yeast residue 13a in the alcoholic fermentation vessel 12 is discharged from a yeast-residue discharge line $L_{12}$. A distillation residue 15a in the distillation column 15 is discharged through a distillation-residue discharge line $L_{14}$.

The biomass hydrothermally-treated product 20 refers to a treated product obtained by hydrothermally decomposing a biomass feedstock by a hydrothermal decomposition device. Particularly, a cellulosic biomass feedstock is hydrothermally decomposed by the hydrothermal decomposition device, thereby obtaining the biomass hydrothermally-treated product 20 by extracting minerals and mineral salts abundantly contained in cellulosic biomass from a solid phase (biomass) to a liquid phase. Details of the hydrothermal decomposition device are described later.

For example, as the cellulosic biomass feedstock, rice straw, wheat straw, corn stover (cornstalk), corn cob (corn core), and EFB (empty fruit brunch of oil palm tree) can be exemplified. However, the present invention is not limited thereto.

In the present invention, not only a hydrothermally extracted fraction but also a solid residual fraction from the hydrothermal decomposition device can be supplied to the alcoholic fermentation vessel 12.

This is because minerals and mineral salts are not extracted into the hydrothermally extracted fraction and remain in the solid residual fraction, and thus minerals and mineral salts are efficiently used.

As minerals and mineral salts referred to in the present invention, nitrogen, phosphorus, sulfur, calcium, magnesium, iron, nickel, cobalt, chromium, zinc, copper, manganese, selenium, molybdenum, boron, and the like can be exemplified, which are contained in the biomass hydrothermally-treated product and supplied to the alcoholic fermentation vessel.

As a result, the biomass hydrothermally-treated product 20 of either one or both of the hydrothermally extracted fraction and the solid residual fraction from the hydrothermal decomposition device are added, thereby enabling to increase the concentration of minerals and mineral salts at the time of alcoholic fermentation, and improve the alcoholic fermentation rate.

Figure 2:
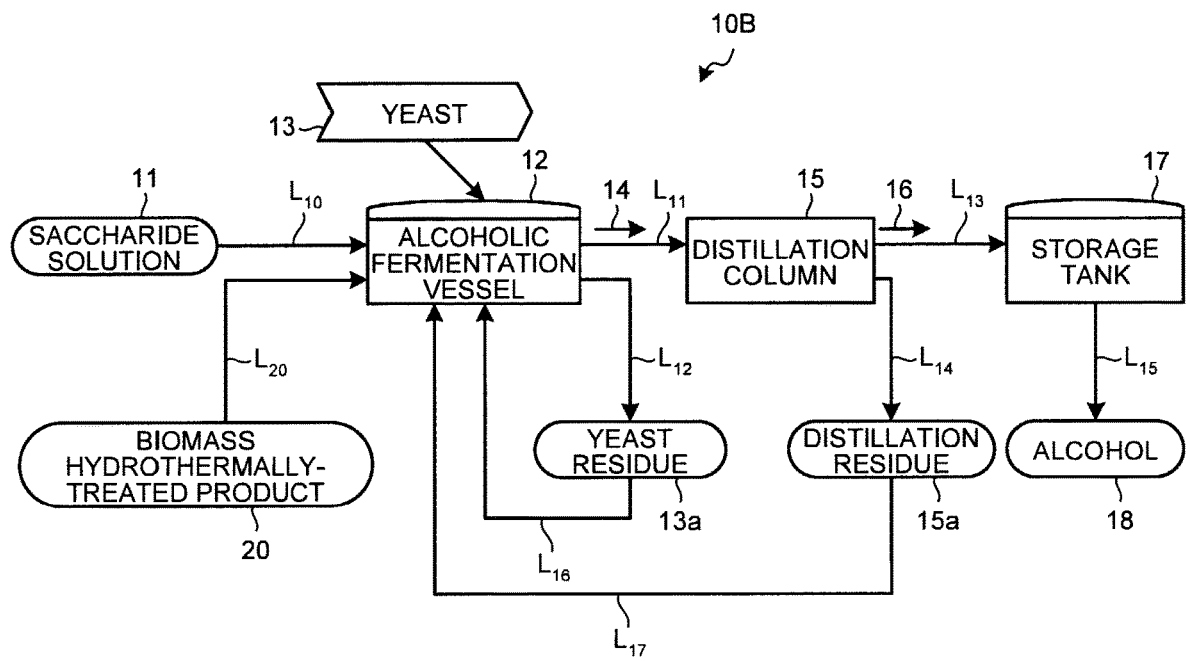
FIG. 2 is a schematic diagram of another alcohol production system according to the first embodiment.

FIG. 2 is a schematic diagram of another alcohol production system according to the present embodiment.

As shown in FIG. 2, an alcohol production system 10B according to the first embodiment further includes addition pipings $L_{16}$ and $L_{17}$ for adding the yeast residue 13a as an alcohol fermentation residual fraction, and the distillation residue 15a as a distillation residual fraction to the alcoholic fermentation vessel, in the alcohol production system according to the first embodiment.

Therefore, minerals and mineral salts remaining in the yeast residue 13a and the distillation residue 15a can be efficiently used. Accordingly, by adding the yeast residue 13a and the distillation residue 15a in addition to the biomass hydrothermally-treated product 20, the concentration of minerals and mineral salts at the time of alcoholic fermentation can be increased and the alcoholic fermentation rate can be improved.

In the present embodiment, the yeast residue 13a and the distillation residue 15a are added simultaneously. However, the present invention is not limited thereto, and only one of the yeast residue 13a and the distillation residue 15a can be added.

Figure 3:
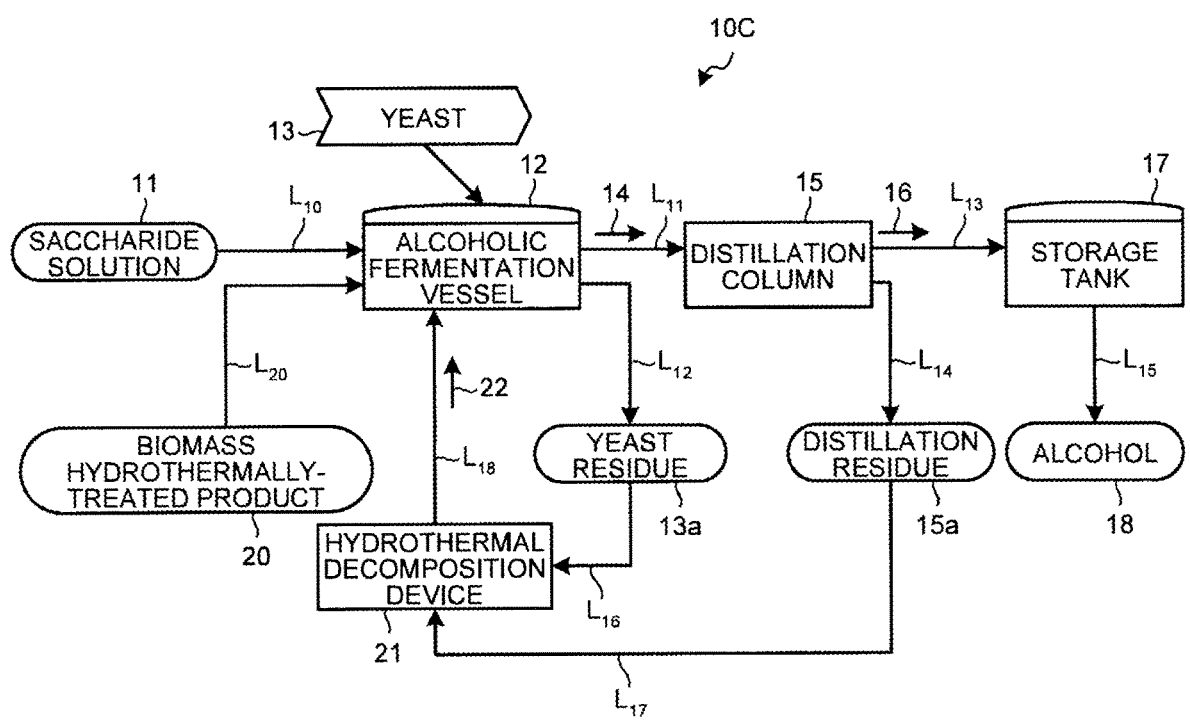
FIG. 3 is a schematic diagram of another alcohol production system according to the first embodiment.

FIG. 3 is a schematic diagram of another alcohol production system according to the present embodiment.

As shown in FIG. 3, an alcohol production system 10C according to the first embodiment includes a hydrothermal decomposition device 21 that hydrothermally decomposes the yeast residue 13a and the distillation residue 15a in the alcohol production system 10B shown in FIG. 2.

The hydrothermal decomposition device 21 can extract minerals and mineral salts remaining in the yeast residue 13a and the distillation residue 15a into a hot water side and supply a hydrothermally treated product 22, which is a hydrothermal extract thereof, to the alcoholic fermentation vessel 12 through an addition piping $L_{18}$, to increase the concentration of minerals and mineral salts at the time of alcoholic fermentation and improve the alcoholic fermentation rate. At this time, a solid content, which is a reaction residue, can be also supplied together with the hydrothermally treated product 22.

In the present embodiment, a case of alcoholic fermentation in which alcohol as an organic feedstock is fermented by using the saccharide solution 11 is explained. However, the fermentation system and the fermentation method using the saccharide solution according to the present invention are not limited thereto. As a product obtained by fermentation treatment, petroleum substitutes, which become raw materials for chemical products or amino acids, which become food ingredients and feedstuffs, other than alcohol (ethanol, methanol, and the like) as the organic feedstock can be obtained by a fermentation device.

As chemical products derived from the saccharide solution 11, for example, there can be mentioned LPG, automotive fuel, aircraft jet fuel, kerosene petroleum, diesel oil, various types of heavy oil, fuel gas, naphtha, ethylene glycol as a naphtha cracked product, ethanolamine, lactic acid, alcohol ethoxylate, vinyl chloride polymer, alkylaluminium, PVA, vinyl acetate emulsion, polystyrene, polyethylene, polypropylene, polycarbonate, MMA resin, nylon, and polyester. Accordingly, a saccharide solution derived from biomass can be efficiently used as a substitute of chemical products derived from crude oil, which is depleting fuel, and raw materials for producing the substitute.

Second Embodiment

Figure 4:
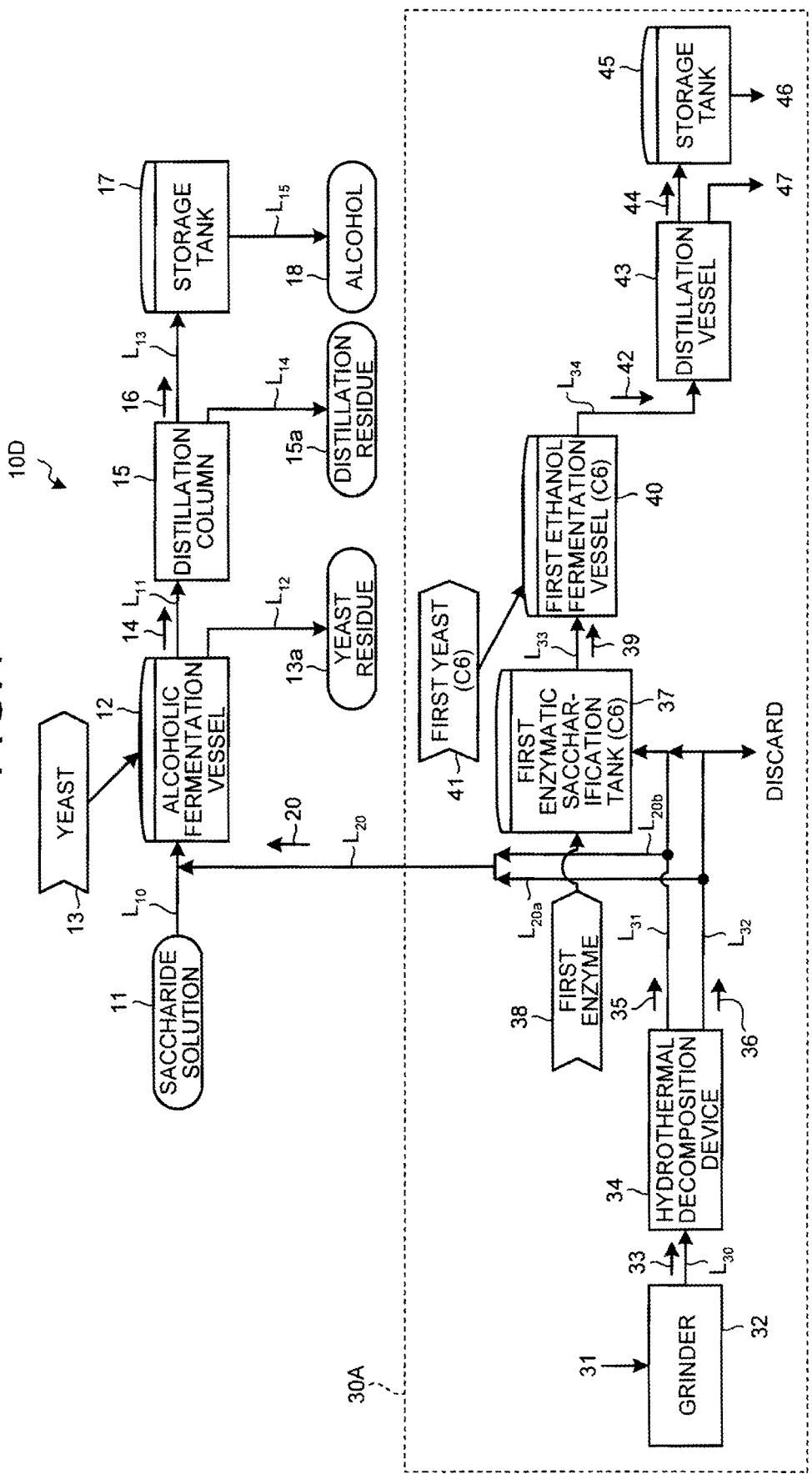
FIG. 4 is a schematic diagram of an alcohol production system according to a second embodiment.

An alcohol production system and an alcohol production method according to another embodiment of the present invention are explained with reference to the drawings. FIG. 4 is a schematic diagram of the alcohol production system.

As shown in FIG. 4, in an alcohol production system 10D according to a second embodiment, the biomass hydrothermally-treated product 20 is a saccharified feedstock (a solid residual fraction 35 or a hydrothermally extracted fraction 36) for an alcohol production system 30A using a cellulosic biomass feedstock 31.

The alcohol production system 30A using the cellulosic biomass feedstock 31 includes a grinder 32 that grounds the cellulosic biomass feedstock 31, a hydrothermal decomposition device 34 that hydrothermally decomposes a biomass-feedstock ground product 33 while feeding the biomass-feedstock ground product 33 into countercurrent contact with pressurized hot water, and transfers a lignin component and a hemicellulose component into pressurized hot water, to separate the lignin component and the hemicellulose component from a biomass solid, a first enzymatic saccharification tank (C6) 37 in which cellulose in the solid residual fraction 35 discharged from the hydrothermal decomposition device 34 is enzymatically treated with a first enzyme (cellulase) 38 to obtain a first saccharide solution 39 containing hexose, a first ethanol fermentation treatment vessel (C6) 40 for producing alcohol by fermentation treatment using first yeast (C6) 41, by using the first saccharide solution (hexose) 39 obtained in the first enzymatic saccharification tank 37, and a distillation vessel 43 for refining a first alcoholic fermentation liquor 42 to separate the first alcoholic fermentation liquor 42 into ethanol 46, which is a distillate 44 as a target product, and a distillation residue 47. Reference sign 45 denotes a storage tank, and $L_{30}$ to $L_{34}$ denote supply pipings.

The solid residual fraction 35 and the hydrothermally extracted fraction 36 from the alcohol production system 30A using the cellulosic biomass feedstock 31 are supplied to the side of the alcoholic fermentation vessel 12 through supply pipings $L_{20a}$ and $L_{20b}$, and mixed with each other along the way and added to the alcoholic fermentation vessel 12 through the piping $L_{20}$.

As a result, by adding the biomass hydrothermally-treated product 20 of either one or both of the solid residual fraction 35 and the hydrothermally extracted fraction 36 from the hydrothermal decomposition device 34, the concentration of minerals and mineral salts at the time of alcoholic fermentation can be increased, and the alcoholic fermentation rate can be improved. The hydrothermally extracted fraction 36 can be discarded or can be supplied to the enzymatic saccharification tank 37. When the hydrothermally extracted fraction 36 is supplied to the enzymatic saccharification tank 37, after the first saccharide solution (hexose) 39 is obtained from the solid residual fraction 35, ethanol can be obtained, and after a hemicellulose component transferred into the hydrothermally extracted fraction 36 is treated with a second enzyme to obtain a saccharide solution containing pentose, ethanol can be obtained.

An example of the hydrothermal decomposition device 34 is explained here.

Figure 5:
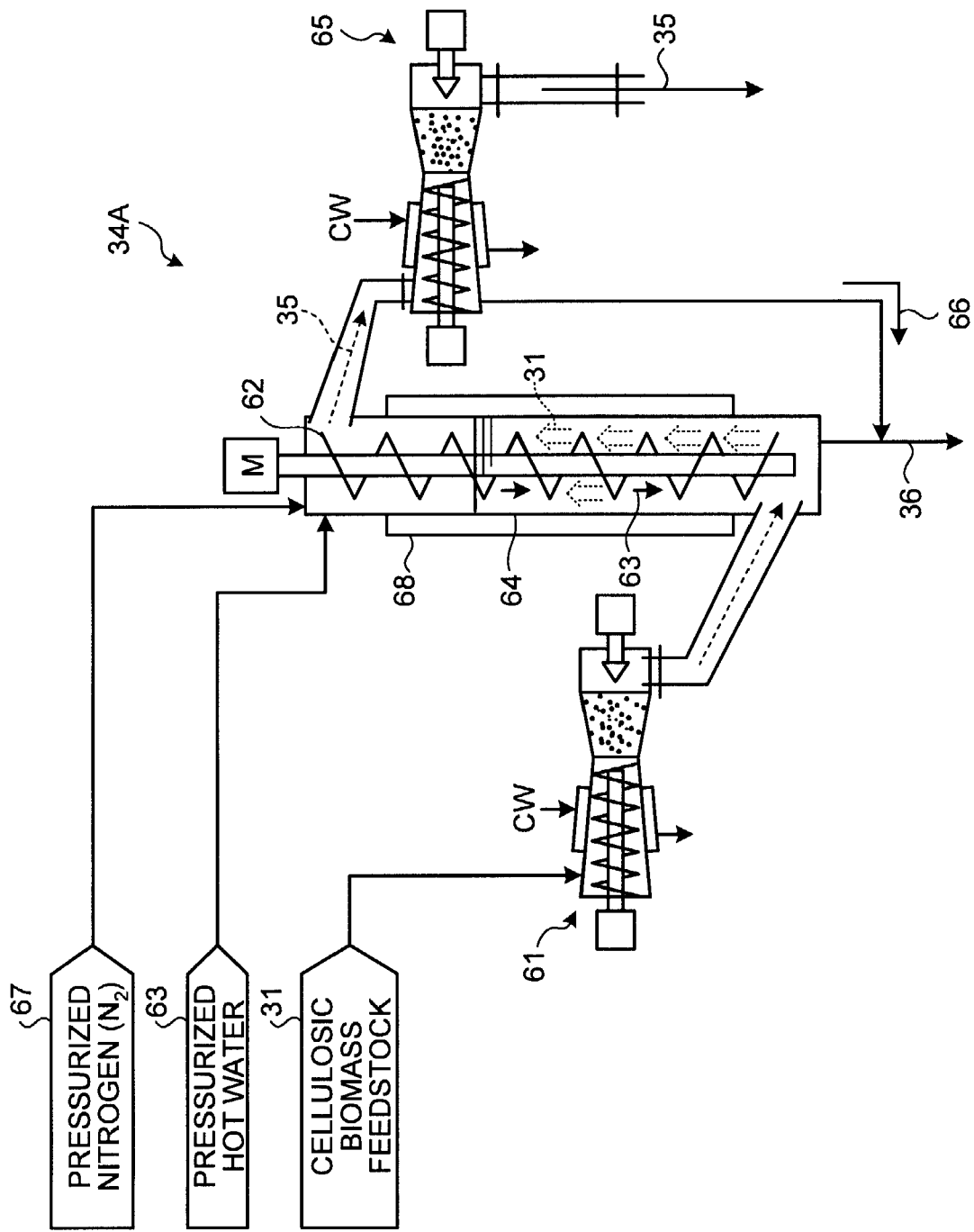
FIG. 5 is a conceptual diagram of a biomass hydrothermal-decomposition device according to the embodiment.

FIG. 5 is a conceptual diagram of a biomass hydrothermal-decomposition device according to the present embodiment.

As shown in FIG. 5, a biomass hydrothermal decomposition device 34A according to the present embodiment includes a biomass supply device 61 that supplies the cellulosic biomass feedstock (hereinafter, "biomass feedstock") 31 under from a normal pressure to an increased pressure, a reactor 64 that transports the supplied biomass feedstock 31 from one side (a lower side in the present embodiment) to the other side (an upper side) inside the device body by a screw means 62, supplies pressurized hot water 63 from the other side (an upper side) different from a supply port of the biomass feedstock 31 into the device body, hydrothermally decomposes the biomass feedstock 31 while feeding the biomass feedstock 31 and the pressurized hot water 63 into countercurrent contact with each other, and transfers a lignin component and a hemicellulose component into the hydrothermally extracted fraction 36, which is pressurized hot water to be discharged, to separate the lignin component and the hemicellulose component from the biomass feedstock 31, and a biomass discharge device 65 that discharges the solid residual fraction 35 as a solid content of biomass from the other side of the device body under from an increased pressure to a normal pressure. In FIG. 5, reference sign 66 denotes a dehydrated solution, 67 denotes pressurized nitrogen, and 68 denotes a temperature jacket.

In the present embodiment, the biomass feedstock 31 is supplied from the lower side. However, the present invention is not limited thereto, and the biomass feedstock 31 can be supplied from the upper side, and at this time, the pressurized hot water 63 is supplied from the lower side.

As the biomass supply device 61 that supplies the biomass feedstock 31 under from a normal pressure to an increased pressure, for example, a screw feeder, a piston pump, and a slurry pump can be mentioned.

The hydrothermal decomposition device 34A is a vertical device in the present embodiment. However, the present invention is not limited thereto, and the hydrothermal decomposition device 34A can be an inclined device or a horizontal reactor.

The reason why the hydrothermal decomposition device 34A is formed as a vertical device or an inclined device is that gas generated in hydrothermal decomposition reaction and gas brought with the biomass feedstock can be discharged from the upper side quickly, which is preferable. Because a decomposition product is extracted by the pressurized hot water 63, the concentration of the extracted product increases from above downward, which is preferable from the viewpoint of extraction efficiency.

The biomass is not particularly limited to any type of material, and refers to accumulation of organisms or organic matters derived from organisms integrated in the circulatory system of materials of the global biosphere (see Japanese Industrial Standards Committee, "Biotechnology-Vocabulary", JIS K 3600 1258, Oct. 1, 2010). However, in the present invention, it is particularly preferable to use a woody material, for example, hardwood and herbaceous lignocellulose resources, agricultural waste, and food waste.

Although the grain diameter of the biomass feedstock 31 is not particularly limited to any size, it is preferred that the biomass feedstock 31 is ground to 5 millimeters or less.

In the present embodiment, before supply of biomass, pretreatment can be performed by using a grinder as a pretreatment device, for example. In addition, biomass can be cleaned by a cleaning device.

When rice husk is used as the biomass feedstock 31, the biomass feedstock 31 can be supplied directly to the hydrothermal decomposition device 34A without being ground.

It is preferred that the reaction temperature in the hydrothermal decomposition device 34A is in a range from 180 to 240° C., and more preferably from 200 to 230° C.

This is because the hydrothermal decomposition rate is low at a temperature lower than 180° C. and a long decomposition time is required, leading to a size increase of the device, which is not preferable. On the other hand, at a temperature exceeding 240° C., the decomposition rate becomes excessive, thereby increasing transfer of the cellulose component from a solid side to a liquid side and promoting excessive decomposition of hemicellulose saccharide, which is not preferable.

The hemicellulose component starts to dissolve at a temperature of about 140° C., cellulose starts to dissolve at a temperature of about 230° C., and the lignin component starts to dissolve at a temperature of about 140° C. However, it is preferred to set the temperature in a range from 180° C. to 240° C. at which cellulose remains on the solid side and the hemicellulose component and the lignin component have a sufficient decomposition rate.

Furthermore, it is preferable to set the reaction pressure to a pressure higher than a saturated vapor pressure of water at each temperature by 0.1 to 0.5 megapascal, at which the inside of the body becomes a pressurized hot water state.

It is also preferable that the reaction time is 20 minutes or less, and more preferably, from 3 minutes to 10 minutes. This is because if the reaction is performed too long, a rate of excessive decomposition products increases, which is not preferable.

In the present invention, it is preferable that the flowage of the pressurized hot water 63 and the biomass feedstock 31 in the body of the hydrothermal decomposition device 34A is a so-called "countercurrently contacted", in which the biomass feedstock 31 and the pressurized hot water 63 are brought into contact with each other, stirred, and caused to flow in countercurrent contact with each other.

In the hydrothermal decomposition device 34A, the solid content of the biomass feedstock 31 is supplied from the bottom side, while the pressurized hot water 63 is supplied from the top side, and each moves opposite to each other. Accordingly, the pressurized hot water 63 (hot water, a solution in which the decomposition product is dissolved) moves while seeping into solid particles, in a counterflow with respect to the biomass feedstock 31 as solids.

At the time of the countercurrent contact with each other, when the biomass feedstock 31 as solids is decomposed by the pressurized hot water 63, the decomposition product thereof is dissolved and transferred to the side of the pressurized hot water 63, and at this time, minerals and mineral salts are eluted.

In the present invention, there is a gaseous portion in the reactor 64, and thus the pressurized nitrogen ($N_2$) 67 is supplied to the inside thereof.

The temperature of the biomass feedstock 31 in the hydrothermal decomposition device 34A can be increased by direct heat exchange, by feeding the biomass feedstock 31 into contact with the pressurized hot water 63 in the device body. The temperature of the biomass feedstock 31 can be increased by using steam or the like from outside, as required.

In the present invention, discharge of components is started sequentially from a component easily solubilized in the pressurized hot water 63 by feeding the biomass feedstock 31 and the pressurized hot water 63 into countercurrent contact with each other, and a temperature gradient occurs from an input portion of the biomass feedstock 31 to an input portion of the hot water, thereby suppressing excessive decomposition of the hemicellulose component, and as a result, pentose components can be recovered efficiently.

Furthermore, by feeding the biomass feedstock 31 and the pressurized hot water 63 into countercurrent contact with each other, heat recovery can be performed, which is preferable from the viewpoint of system efficiency.

Figure 6:
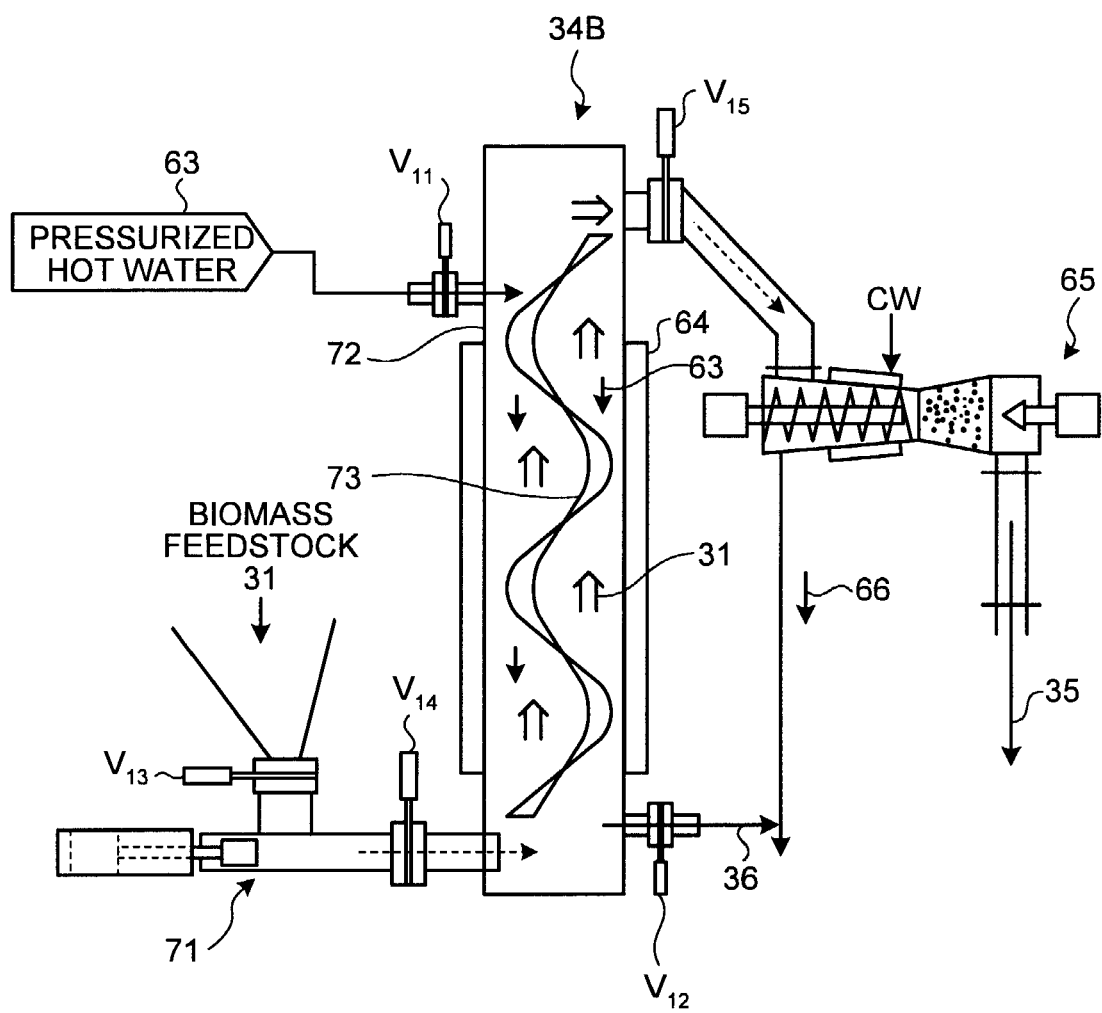
FIG. 6 is a conceptual diagram of another biomass hydrothermal-decomposition device according to the embodiment.

FIG. 6 is a conceptual diagram of another biomass hydrothermal-decomposition device according to the present embodiment. As shown in FIG. 6, a biomass hydrothermal decomposition device 34B according to the present embodiment includes a biomass supply device 71 that supplies a biomass feedstock (in the present embodiment, for example, wheat straw) 31 under from a normal pressure to an increased pressure, a reactor 72 that gradually moves the supplied cellulosic biomass feedstock 31 from one end of upper and lower ends (a lower end in the present embodiment) inside a vertical device body (hereinafter, "device body") in a consolidation state, supplies pressurized hot water 63 from the other end (an upper end in the present embodiment) different from the supply port of the biomass feedstock 31 into the device body, hydrothermally decomposes the biomass feedstock 31 while feeding the biomass feedstock 31 and the pressurized hot water 63 into countercurrent contact with each other, and transfers a lignin component and a hemicellulose component into the pressurized hot water 63, to separate the lignin component and the hemicellulose component from the biomass feedstock 31, and the biomass discharge device 65 that discharges the solid residual fraction 35 as a solid content of biomass from the supply port side of the pressurized hot water 63 of the device body under from an increased pressure to a normal pressure. Reference signs $V_{11}$ to $V_{15}$ denote ON-OFF valves.

As the biomass supply device 71 that supplies biomass under from a normal pressure to an increased pressure, for example, a pumping means such as a piston pump and a slurry pump can be mentioned.

In the present embodiment, a fixed stirring means 73 that stirs the biomass feedstock 31 in a consolidation state of a so-called "plug flow" is provided in the device body, so that the biomass feedstock 31 fed into the device body is stirred by a stirring function or behavior at the time of moving the biomass feedstock 31 fed therein in an axial direction.

By providing the fixed stirring means 73, mixing with the pressurized hot water 63 on a solid surface and in the solid advances, thereby promoting the reaction.

In the present invention, it is preferable such that the flowage of the pressurized hot water 63 and the biomass feedstock 31 in the device body of the hydrothermal decomposition device 34B is a so-called "counterflow", in which the biomass feedstock 31 and the pressurized hot water 63 are brought into contact with each other, stirred, and caused to flow in countercurrent contact with each other.

Because the hydrothermal decomposition device 34B performs hydrothermal decomposition by the plug flow method, the configuration thereof is simple, and the biomass feedstock 31 as a solid moves parallel to a tube central axis, while being stirred vertically with respect to the tube central axis. Meanwhile, the pressurized hot water 63 (hot water, a solution in which the decomposition product is dissolved) moves while seeping into solid particles, in a counterflow with respect to the solid.

In the plug flow, a uniform flow of the pressurized hot water 63 can be realized. This is because when the biomass feedstock 31 as a solid is dissolved by the pressurized hot water 63, the decomposition product dissolves on the hot water side. The vicinity of the decomposition product has a high viscosity, and hot water preferentially moves to the vicinity of an undecomposed portion, to decompose the undecomposed portion subsequently. Accordingly, hot water flows uniformly to realize uniform decomposition.

Furthermore, due to the tube wall resistance on an inner surface of the device body in the hydrothermal decomposition device 34B, the solid density on an outlet side of the biomass feedstock 31 decreases more as compared to that on an inlet side of the biomass feedstock 31 in the device body. In addition, because the solid residual fraction 35, which is a solid content of biomass, decreases due to decomposition, the percentage of the pressurized hot water 63 increases, and a decomposition component in a liquid is excessively decomposed due to an increase in a liquid residence time. Accordingly, at least the fixed stirring means 73 is provided.

Third Embodiment

Figure 7:
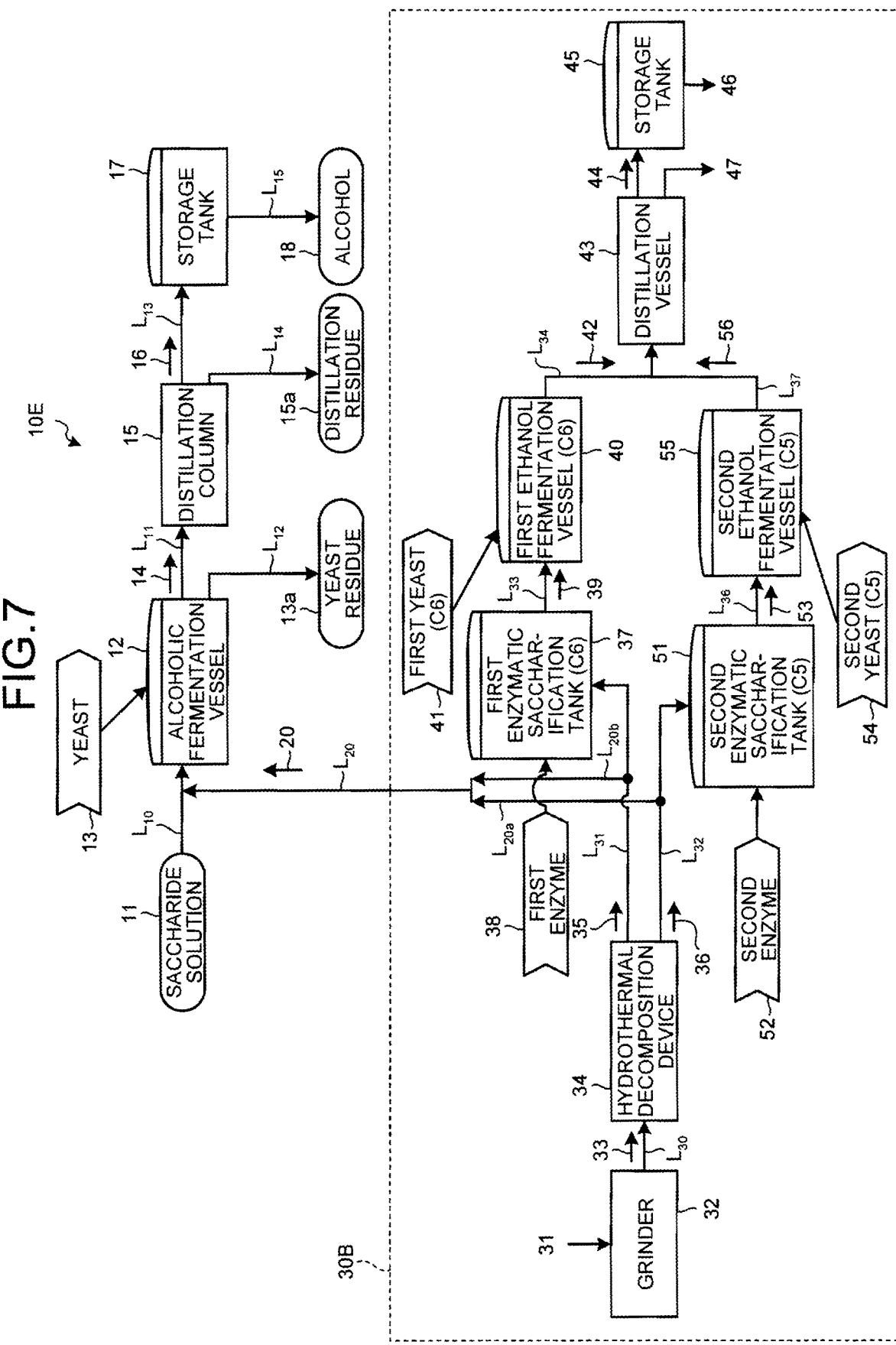
FIG. 7 is a schematic diagram of an alcohol production system according to a third embodiment.

An alcohol production system and an alcohol production according to another embodiment of the present invention are explained with reference to the drawings. FIG. 7 is a schematic diagram of an alcohol production system according to a third embodiment.

As shown in FIG. 7, an alcohol production system 10E according to the third embodiment produces alcohol from the hydrothermally extracted fraction 36 of the saccharified feedstock in an alcohol production system 30B using the cellulosic biomass feedstock 31, in the system of the second embodiment.

That is, the alcohol production system 10E includes a second enzymatic saccharification tank 51 in which a hemicellulose component transferred to the hydrothermally extracted fraction 36 discharged from the hydrothermal decomposition device 34 in the alcohol production system 30B using the cellulosic biomass feedstock 31 is treated with a second enzyme 52 to obtain a saccharide solution 53 containing pentose, and a second ethanol fermentation vessel 55 for producing alcohol by fermentation treatment using second yeast (C5) 54, by using the second saccharide solution (pentose) 53 obtained in the second enzymatic saccharification tank 51, to produce ethanol 46, which is the distillate 44 as a target product, by refining a second alcoholic fermentation liquor 56. Reference signs $L_{36}$ to $L_{37}$ denote supply pipings.

Figure 8:
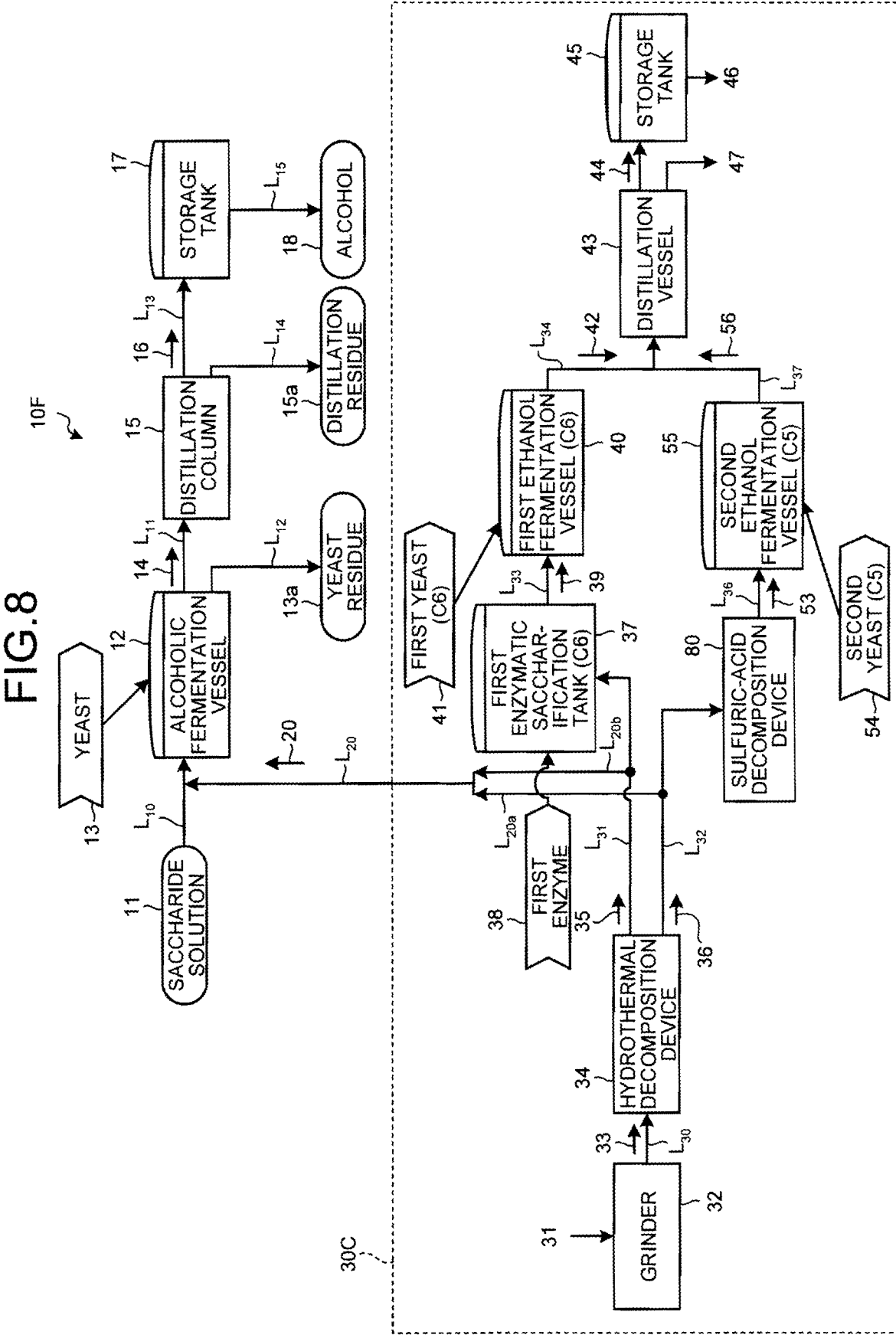
FIG. 8 is a schematic diagram of another alcohol production system according to the third embodiment.

FIG. 8 is a configuration diagram of an alcohol production system using another cellulosic biomass feedstock.

As shown in FIG. 8, another alcohol production system 10F according to the third embodiment performs saccharification by sulfuric acid decomposition, as a method other than saccharification with an enzyme, at the time of saccharification of the hydrothermally extracted fraction 36 in an alcohol production system 30C using the cellulosic biomass feedstock 31. That is, a sulfuric-acid decomposition device 80 is used, which supplies sulfuric acid to the hydrothermally extracted fraction 36, to decompose the hemicellulose component in the hydrothermally extracted fraction 36 with sulfuric acid into the second saccharide solution 53 containing pentose.

As decomposition conditions in the sulfuric-acid decomposition device 80 according to the present invention, the sulfuric acid concentration is from 0.1 to 5% by weight, preferably from 1 to 4% by weight, a decomposition temperature is from 100 to 140° C., preferably about 120° C., and a decomposition time is from 30 minutes to 3 hours, preferably about 1 hour. This is because, if these numbers are outside the above ranges, excellent decomposition of hemicellulose cannot be performed.

Fourth Embodiment

Figure 9:
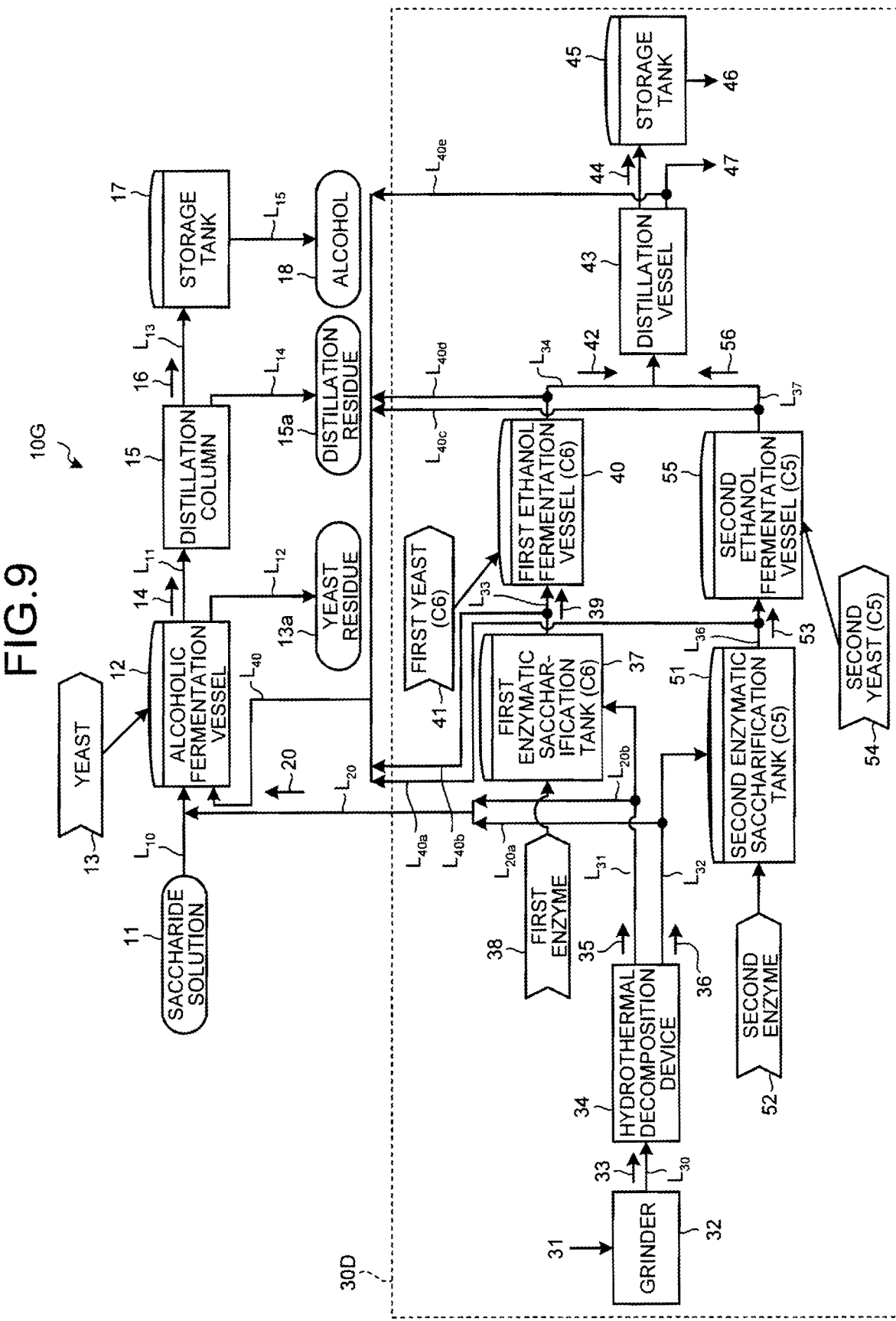
FIG. 9 is a schematic diagram of another alcohol production system according to the fourth embodiment.

An alcohol production system and an alcohol production according to another embodiment of the present invention are explained with reference to the drawings. FIG. 9 is a schematic diagram of an alcohol production system according to a fourth embodiment.

As shown in FIG. 9, an alcohol production system 10G according to the fourth embodiment uses a treatment residue from an alcohol production system 30D using the cellulosic biomass feedstock 31.

As shown in FIG. 9, the solid residual fraction 35 and the hydrothermally extracted fraction 36 from the alcohol production system 30D using a cellulosic biomass feedstock are supplied to the side of the alcoholic fermentation vessel 12 through supply pipings $L_{20a}$ and $L_{20b}$, mixed with each other along the way, and added to the alcoholic fermentation vessel 12 through the piping $L_{20}$. At the same time, the first saccharide solution (hexose) 39, the first alcoholic fermentation liquor 42, the distillation residue 47, the second saccharide solution (pentose) 53, and the second alcoholic fermentation liquor 56 are respectively supplied to the side of the alcoholic fermentation vessel 12 through pipings $L_{40a}$, $L_{40b}$, $L_{40c}$, $L_{40d}$, and $L_{40e}$. These are mixed with each other along the way and at least one treated product is added into the alcoholic fermentation vessel 12.

Figure 10:
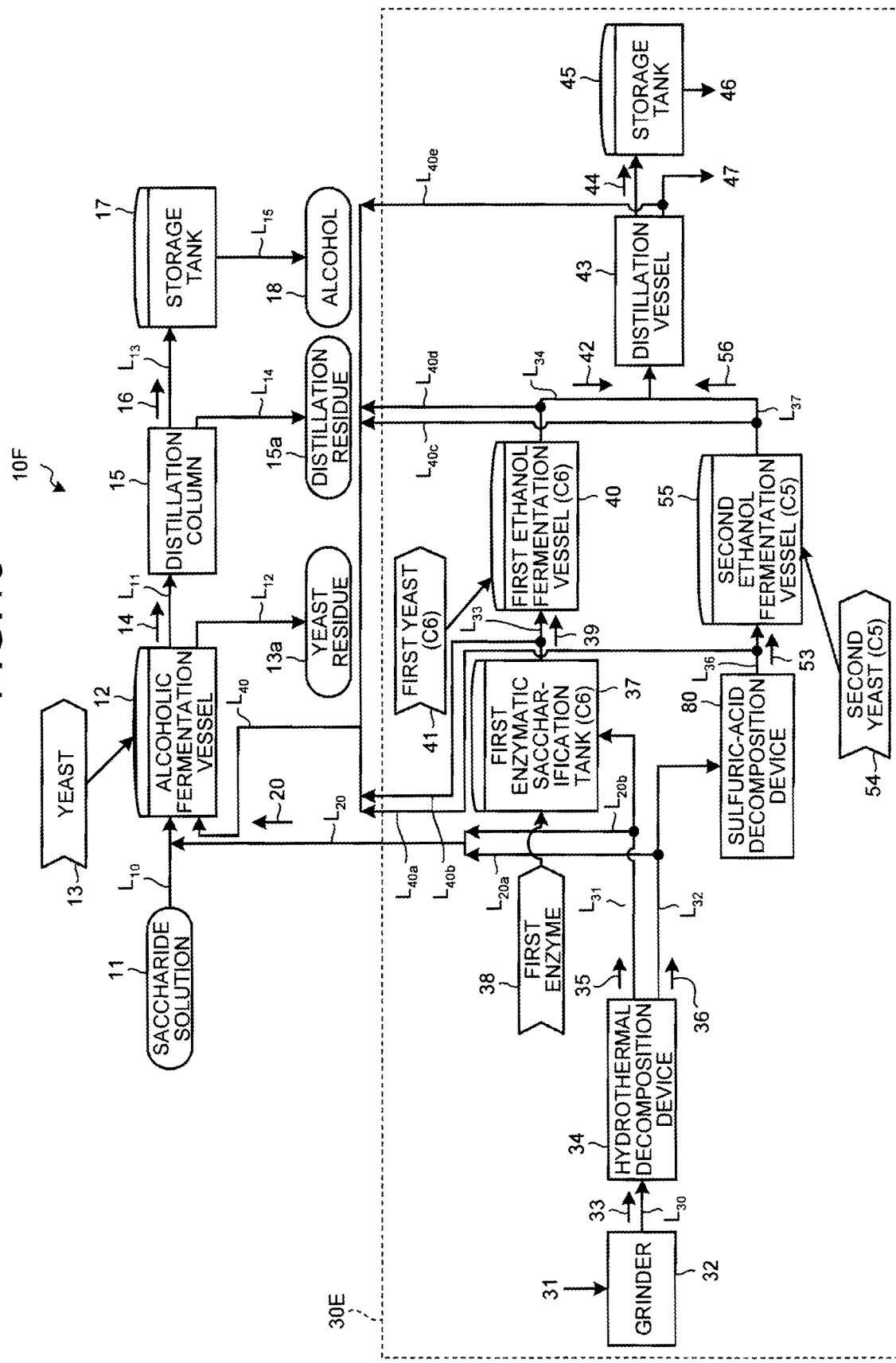
FIG. 10 is a schematic diagram of another alcohol production system according to the fourth embodiment.

Another alcohol production system 10F according to the fourth embodiment shown in FIG. 10 uses a treatment residue from an alcohol production system 30E using the cellulosic biomass feedstock 31.

As shown in FIG. 10, the solid residual fraction 35 and the hydrothermally extracted fraction 36 from the alcohol production system 30E using a cellulosic biomass feedstock are supplied to the side of the alcoholic fermentation vessel 12 through the supply pipings $L_{20a}$ and $L_{20b}$, mixed with each other along the way, and added to the alcoholic fermentation vessel 12 through the piping $L_{20}$. At the same time, the first saccharide solution (hexose) 39, the first alcoholic fermentation liquor 42, the distillation residue 47, the second saccharide solution (pentose) 53, and the second alcoholic fermentation liquor 56 are respectively supplied to the side of the alcoholic fermentation vessel 12 through the pipings $L_{40a}$, $L_{40b}$, $L_{40c}$, $L_{40d}$, and $L_{40e}$. These are mixed with each other along the way and at least one treated product is added into the alcoholic fermentation vessel 12.

As a result, by circulating the first saccharide solution (hexose) 39, the first alcoholic fermentation liquor 42, the distillation residue 47, the second saccharide solution (pentose) 53, and the second alcoholic fermentation liquor 56 from the alcohol production system 30D or 30E using a cellulosic biomass feedstock in the alcoholic fermentation vessel 12, the concentration of minerals and mineral salts in alcoholic fermentation can be increased, and the alcoholic fermentation rate can be improved. At the same time, the amount of minerals and mineral salts added from outside of the system can be decreased.

In the present embodiment, as a target product of the fermentation treatment by the alcohol production systems 30A to 30E using the cellulosic biomass feedstock 31, ethanol of alcohol, which is an organic feedstock, has been exemplified. However, the present invention is not limited thereto, and petroleum substitutes, which become raw materials for chemical products or amino acids, which become food ingredients and feedstuffs, other than alcohol can be obtained by the fermentation device.

As the chemical products derived from a saccharide solution, for example, there can be mentioned LPG, automotive fuel, aircraft jet fuel, kerosene petroleum, diesel oil, various types of heavy oil, fuel gas, naphtha, ethylene glycol as a naphtha cracked product, ethanolamine, lactic acid, alcohol ethoxylate, vinyl chloride polymer, alkylaluminium, PVA, vinyl acetate emulsion, polystyrene, polyethylene, polypropylene, polycarbonate, MMA resin, nylon, and polyester. Accordingly, the saccharide solution derived from biomass can be efficiently used as a substitute of chemical products derived from crude oil, which is depleting fuel, and raw materials for producing the substitute.

REFERENCE SIGNS LIST 10A to 10H alcohol production system
11 saccharide solution
12 alcoholic fermentation vessel
13 yeast
13a yeast residue
14 alcoholic fermentation liquor
15 distillation column
15a distillation residue
18 alcohol
20 biomass hydrothermally-treated product
30A to 30E alcohol production system using cellulosic biomass feedstock
34 hydrothermal decomposition device
35 solid residual fraction
36 hydrothermally extracted fraction

The invention claimed is:

1. A fermentation method for two saccharide solutions comprising:
- A. hydrothermally treating a first biomass feedstock containing minerals and mineral salts with hot compressed water to extract minerals and mineral salts into the hot water while leaving the cellulose, lignin, and hemicellulose in a treated feedstock;
- B. hydrothermally treating the treated feedstock from step A at a temperature greater than 140° C. to extract the lignin and hemicellulose into the water, while leaving the cellulose in the solid residue;
- C. transferring the solid residue containing cellulose from step B in an enzymatic saccharification tank in order to be enzymatically saccharified to produce a first saccharide solution;
- D. fermenting the first saccharide solution from step C in a fermentation vessel containing yeast to be fermented into a first fermentation liquor;
- E. producing a second saccharide solution from a second biomass feedstock which is materially different from the first biomass feedstock;
- F. transferring the second saccharide solution from step E to a second fermentation vessel containing yeast to produce a second fermentation liquor and a yeast residue, wherein the extracted minerals and mineral salts from step A are added to the second fermentation vessel to improve the fermentation of said second saccharide solution;
- G. distilling the second fermentation liquor from step F in a distillation column producing alcohol and a distillation residue;
- H. combining the yeast residue of step F and the distillation residue of step G into a vessel and hydrothermally decomposing the combination to produce a hydrothermally treated product including minerals and mineral salts; and
- I. directly adding the hydrothermally treated product from step H to the second fermentation vessel in step F.

* * * * *